United States Patent [19]

Kaneko et al.

[11] 4,395,125
[45] Jul. 26, 1983

[54] CENTERING SYSTEM

[75] Inventors: Nobutaka Kaneko, Hachiouji; Toshihide Fujiwara, Fuchu, both of Japan

[73] Assignee: Olympus Optical Co., Ltd., Tokyo, Japan

[21] Appl. No.: 175,415

[22] Filed: Aug. 5, 1980

[30] Foreign Application Priority Data

Aug. 16, 1979 [JP] Japan .................... 54-103612

[51] Int. Cl.³ .................. G01B 11/00; G01N 21/86
[52] U.S. Cl. ........................ 356/400; 250/548
[58] Field of Search ............ 356/375, 400; 250/561, 250/548

[56] References Cited

U.S. PATENT DOCUMENTS 3,313,943  4/1967  Sager ........................ 250/548
3,787,701  1/1974  Thaddey ..................... 250/561
4,204,767  5/1980  Kato et al. .................. 356/444

*Primary Examiner*—William H. Punter
*Attorney, Agent, or Firm*—Cushman, Darby & Cushman

[57] ABSTRACT

A sample centering system comprising a photometric system for colorimetrically measuring samples applied onto a carrier shifted in a definite direction, a detection system arranged at a definite interval apart from said photometric system, a sample detection signal generating means for generating a signal on the basis of the output from said detection system, and a shifting timer which is operated on the basis of said sample detection signal or at a definite time after shifting of said carrier is started, said sample centering system being so adapted as to stop said carrier when said shifting timer is turned off after a definite time, thereby making it possible to stop said carrier always at a time when a sample is located on the optical axis of said photometric system regardless of sample conditions.

2 Claims, 11 Drawing Figures

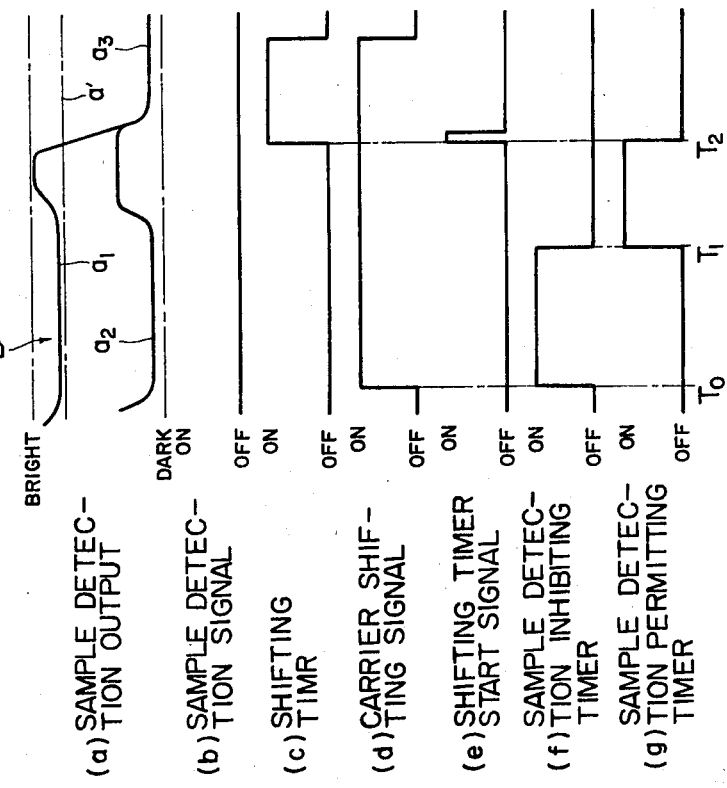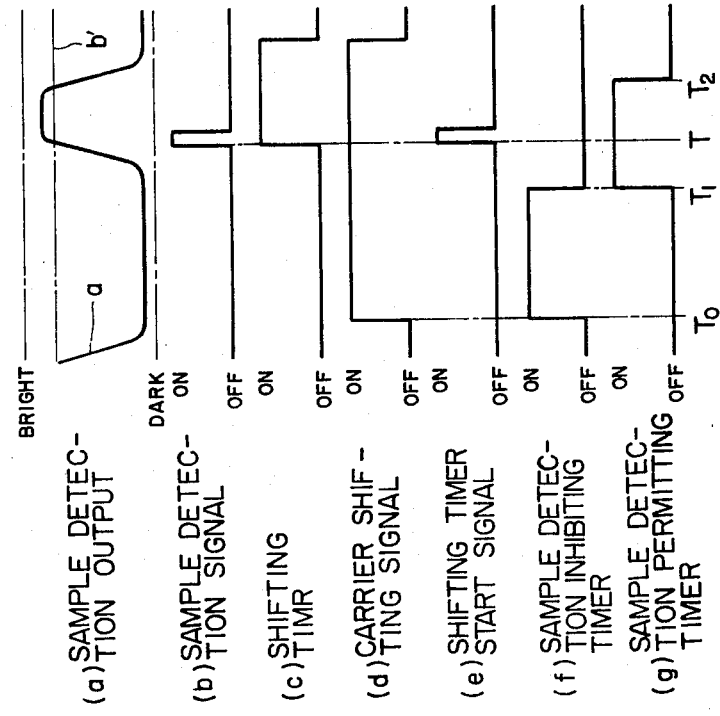

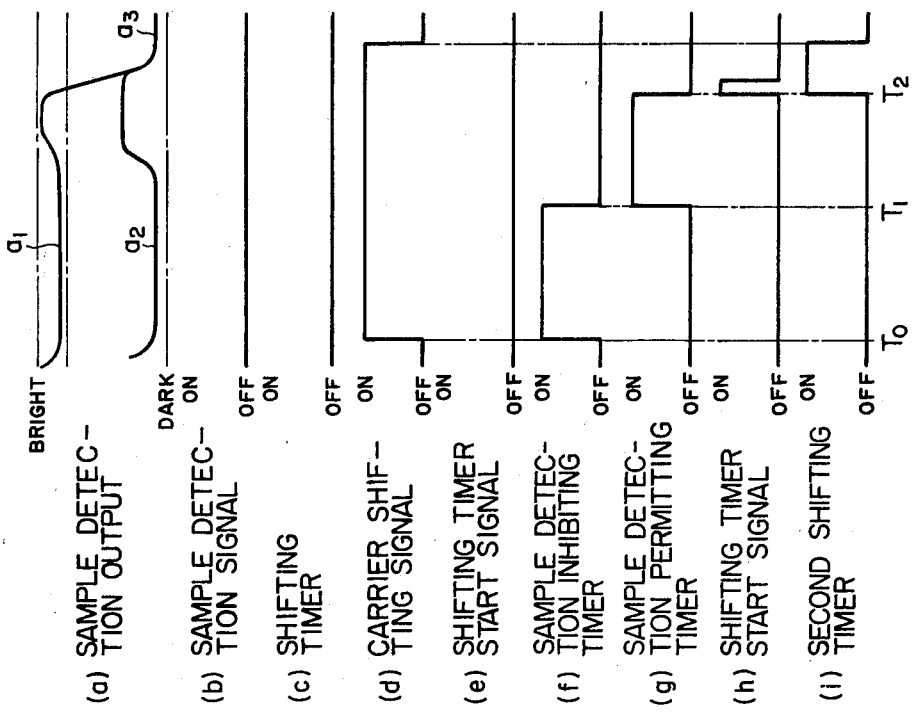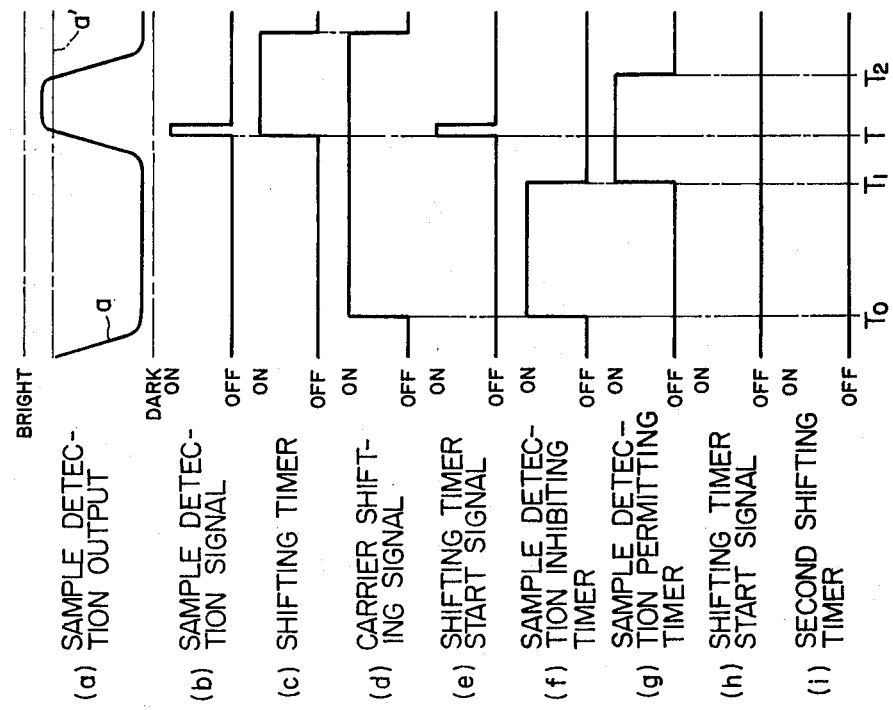

CENTERING SYSTEM

BACKGROUND OF THE INVENTION (a) Field of the Invention

The present invention relates to a sample centering system, and more specifically to a sample centering system for quantitative analyses of fractionated patterns of sera by the electrophoresis.

(b) Description of the Prior Art

In the electrophoresis, samples such as sera are applied onto a carrier made of cellulose acetate or the similar material, the carrier is electrically energized to form fractionated patterns of the samples, the carrier is colored, discolored and made transparent, and then the samples are colorimetrically measured for quantitative determinations. In order to automatically perform the state of colorimetry for quantitative determinations out of these steps for the electrophoresis, the carrier is shifted between a light source and a photo detector, stopped each time a sample is located just between the light source and photo detector, and the sample is scanned for colorimetry by shifting the light source and photo detector as a combination, for example, in the direction perpendicular to the shifting direction of the carrier. For this purpose, it is necessary to detect positions of the samples applied onto the carrier and stopping it each time a sample is located just between the light source and photo detector.

Construction of an example of the conventionally known sample detectors is illustrated in FIG. 1, in which the reference numeral 1 represents a carrier, the reference numeral 2 designates samples applied onto the carrier at definite intervals, the reference numeral 3 denotes a light source assembly for photometry consisting of a light source lamp 4, a lens system 5, a filter 6, a slit 7, etc., the reference numeral 8 represents a photo detector for photometry consisting of a slit 9 and photo detector elements 10, the reference numeral 11 designates a plural number of optical fibers having ends 11a which are arranged under the passage of the carrier in the direction perpendicular to the shifting direction of the carrier as shown in FIG. 2, the reference numeral 12 denotes a light source lamp arranged in the vicinity of the other ends 11b of the optical fibers 11, and the reference numeral 13 represents plural number of photo detector elements which are arranged over the passage of the carrier so as to receive light emerging from the optical fibers. A sample detector system is composed of these optical fibers, photo detector elements and so on. When the carrier 1 is shifted by an adequate shifting means in the direction indicated by arrow A as shown in FIG. 1 in the sample detector having the above-described construction, the rays emerging from the individual optical fibers 11 pass through the carrier 1 and are received by the individual photo detector elements 13. The photo detector elements 13 provide high outputs while transparent portion 1a of the carrier 1 is positioned between the ends 11a of the optical fibers 11 of the sample detector system and the photo detector elements 13, whereas the photo detector elements 13 provide low outputs when the sample 2 applied onto the carrier 1 is located between the ends 11a of the optical fibers 11 and the photo detector elements 13. It is therefore possible to detect position of the sample 2 on the basis of the outputs from the photo detector elements 13. After the position of the sample is detected with the sample detector system, the optical axis of the photometric system consisting of the light source assembly for photometry and the photo detector system for photometry can be aligned with the center of the sample by stopping the carrier 1 after further shifting the carrier 1 for a definite distance determined by the distance as measured from the sample detector system to the photometric system and so on.

Detection of the sample position with the above-described sample detector system will be described with reference to FIG. 3 and FIG. 4. The outputs from the photo detector elements 13 are amplified by an amplifier 14, whose output a is compared, in a comparator detector circuit 16 in a sample detector circuit 15, with a signal a' provided by a threshold level signal generator 17. The signal a' provided by the threshold level signal generator 17 is a signal kept at a preset constant level as shown in FIG. 4. When the comparison between the output a and signal a' indicates coincidence of both the signals, a sample detection signal b is generated. This sample detection signal b functions to turn on a shifting timer 18, which in turn generates a signal c. Since this signal c is turned off in a certain definite time, a carrier shifting signal d already provided from a controller 19 is turned off at the falling time of the signal c. Therefore, a carrier shifting mechanism 20 which is driven by the carrier shifting signal d from the controller 19 is stopped when the signal d is turned off to stop the carrier. When the shifting timer is set for a time interval just for shifting the carrier for a distance 1 shown in FIG. 1, the carrier is stopped the moment that the center of the sample 2 is aligned with the optical axis of the photometric system. In other words, for the above-described example which detects the rear end of the sample with the sample detector system, the shifting distance after detection of the sample to stopping of the carrier is equal to the distance between the photometric system and the detector system minus half the length of the sample in the carrier shifting direction (more strictly, the length as measured from the front end of the sample to the point at which signal level corresponding to the rear end of the sample becomes coincident with the threshold level signal).

In the above-described sample detector, however, the comparator detector circuit 16 does not provide the signal b in case of a sample at such a low concentration that the sample detection output signal $a_1$ is not lowered (darkened) to the threshold level, thereby making it impossible to detect the sample. Further, in case of a sample at such a low concentration that the sample detection output is close to the threshold level, detection is made unstable. On the other hand, in case of a sample at such a high concentration as to provide sample detection signal $a_2$ shown in FIG. 5, the sample is continuous with the neighboring one due to diffusion, whereby the output corresponding to the section between samples $a_2$ and $a_3$ is not higher (brighter) than the threshold level. It is therefore impossible to discriminate the two samples from each other, thereby constituting possibility to judge the two samples as one and proceed to analysis of the next sample without performing photometry of one of the samples $a_2$ and $a_3$. As a result, analytical result of the sample which is not subjected to photometry is not recorded and skipped on a clinical card in transferring clinical data, etc. If such skipping is not noticed in transferring analytical data, correspondence between samples and patients will be erroneous on all the subsequent cards.

SUMMARY OF THE INVENTION

A general object of the present invention is to provide a method and a means for locating the centers of samples substantially on the optical axis of a photometric system by stopping shifting of the carrier a definite time after detection of a sample when a sample detector system combined with a photometric system detects a sample, and stopping shifting of the carrier in a definite time different from the said definite time after starting shifting of the carrier when the sample detector system is incapable of detecting a sample.

BRIEF DESCRIPTION OF THE DRAWINGS

FIG. 7 illustrates a time chart of the individual signals in case of a normal sample in the first embodiment of the present invention;

FIG. 8 illustrates a time chart of the individual signals in case of a sample which is not normal in the first embodiment of the present invention;

FIG. 10 illustrates a time chart of the individual signals in case of a normal sample in the second embodiment of the present invention; and FIG. 11 illustrates a time chart of the individual signals in case of a sample which is not normal in the second embodiment of the present invention.

DETAILED DESCRIPTION OF THE PREFERRED EMBODIMENTS

Figure 1:
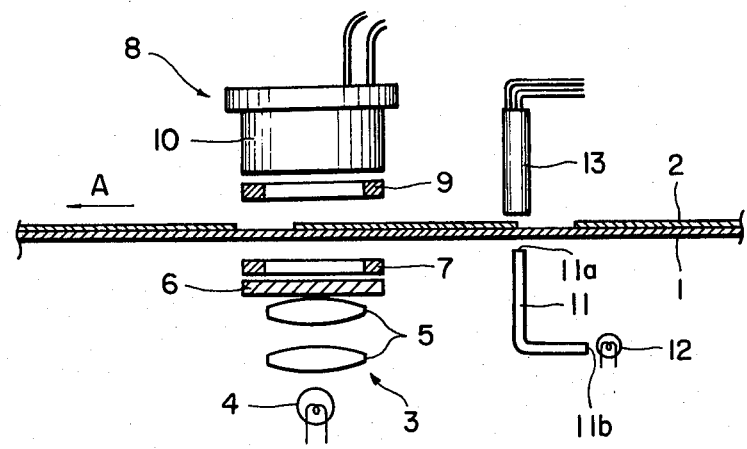
FIG. 1 shows a sectional view illustrating the construction of the conventional sample detector.
Figure 2:
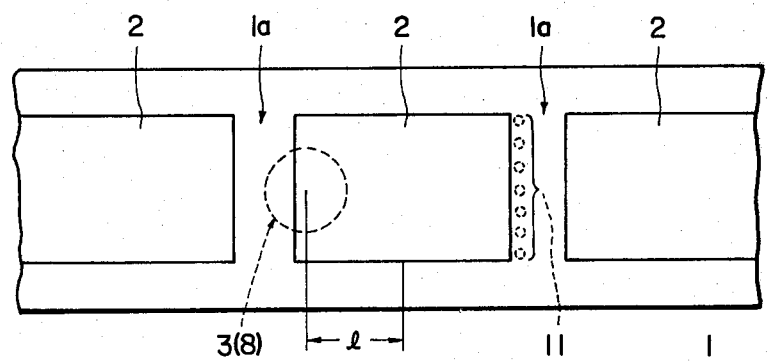
FIG. 2 shows a diagram illustrating the manner of arrangement of samples on a carrier.
Figure 3:
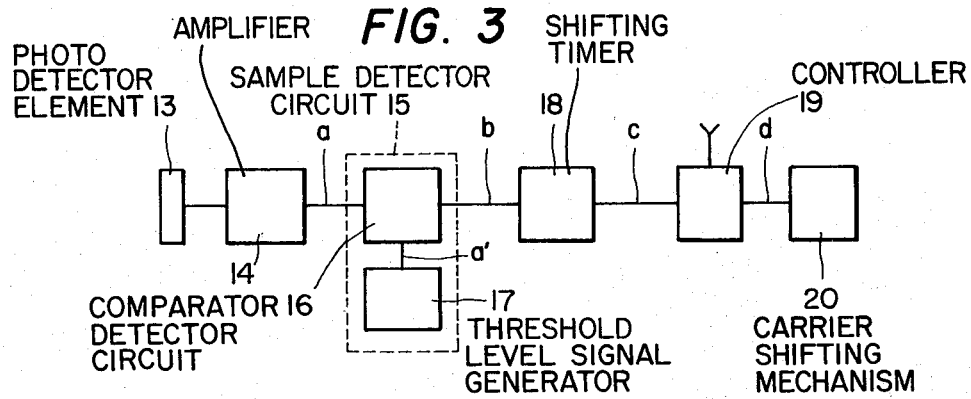
FIG. 3 shows a block diagram of sample detector system used for the conventional sample detecting method.
Figure 4:
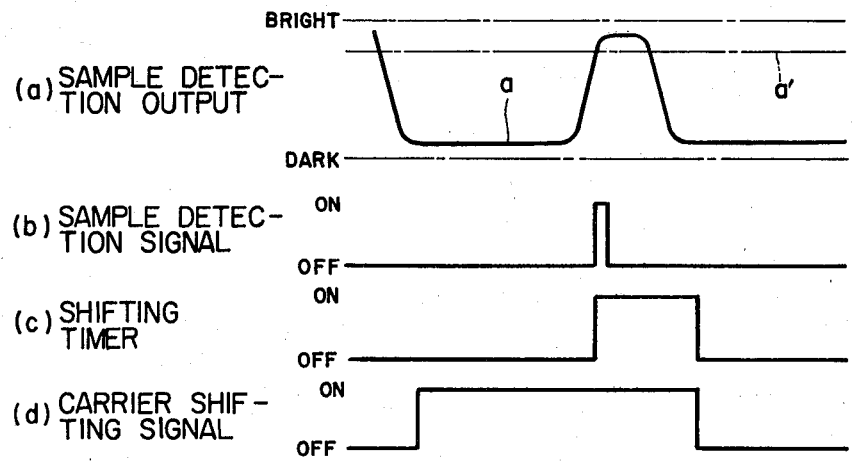
FIG. 4 shows a time chart of the individual signals in the detector system illustrated in FIG. 3.
Figure 5:
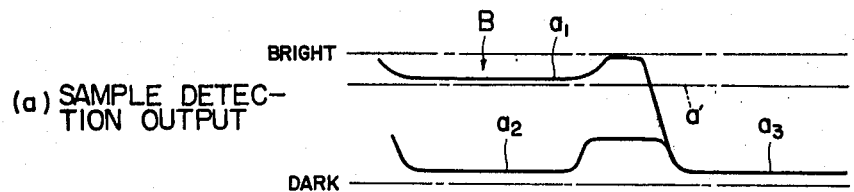
FIG. 5 shows a diagram illustrating concentration distribution of a sample which is not normal.
Figure 6:
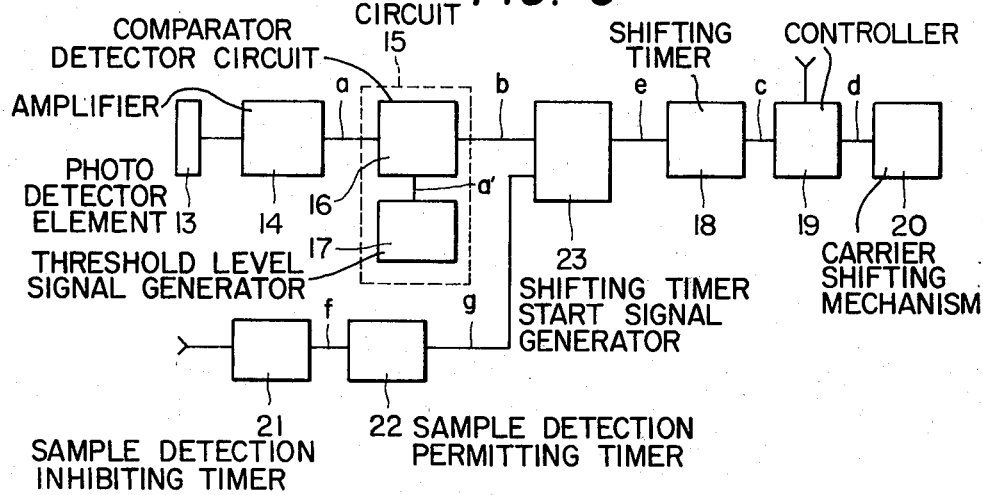
FIG. 6 shows a block diagram of a first embodiment of the present invention.

A block diagram of the detector system used for the detection method according to the present invention is shown in FIG. 6 wherein the photo detector elements 13, amplifier 14, sample detector circuit 15, etc. are substantially same as those illustrated in FIG. 3 and schematically shown with the same reference numerals. The reference numeral 21 represents a sample detection inhibiting timer which is turned on for inhibiting detection of sample. The reference numeral 22 designates a sample detection permitting timer which is turned on at falling time of the signal from the sample detection inhibiting timer and turned off in a definite time. The reference numeral 23 denotes a shifting timer start signal generator which generates a shifting timer start signal e when it receives sample detection signal b from the comparator detector circuit 16 while the sample detection permitting timer 22 is turned on. If the sample detection signal b is not received while the sample detection permitting timer is turned on, the timer start signal is generated when the signal from the sample detection permitting timer is switched from on to off. Upon the generation of the shifting timer start signal e, a signal for the next shifting timer is turned on, and when the shifting timer is switched from on to off, the carrier shifting mechanism 20 is stopped by the carrier shift controller 19 in quite the same manner as that by the conventional method shown in FIG. 3.

Now, sample detection by the method according to the present invention will be described. In the first place, positional detection of a sample in the normal condition will be described with reference to FIG. 7. At time $T_0$, a first shifting signal d is generated to shift the carrier with the carrier shifting mechanism 20. Simultaneously, the sample detection inhibiting timer 21 is turned on. By setting this timer for an adequate time, it is possible to switch the timer from on to off before the rear end of the sample reaches the detector system. At time $T_1$, the signal from the sample detection inhibiting timer 21 changes from on to off and, at the same time, the sample detection permitting timer 22 is turned on. In the section from $T_1$ to $T_2$ where the signal g from the timer 22 is kept on, the sample detection signal a crosses the threshold level a' from the dark side to the bright side of the level a'. The moment that the output of the signal a is coincident with the level a', the comparator detector circuit 16 generates the signal b which in turn functions to allow the shifting timer start signal generator 23 to generate the signal e and turn on the shifting timer. After a definite time lapses, the shifting timer 18 is switched from on to off. At this time, the carrier shifting signal d from the carrier shifting controller 19 is turned off to stop the carrier shifting mechanism 20 and the carrier accordingly. Since the shifting timer is set for a time interval which is equal to the time required for shifting the carrier for a distance of 1, the carrier is stopped at a position at which the center of the sample is aligned with the optical axis of the photometric system. Then, detection of a sample which is not normal will be described with reference to FIG. 8, Out of the two samples $a_1$ and $a_2$ shown in FIG. 8, descriptions will be made first on the sample $a_1$ which is at a lower concentration. In this case, no sample detection signal is produced since output does not become lower (darker) than the threshold level a'. If the sample $a_1$ has a portion at a concentration which is close to the threshold level a' (for example, the portion indicated by symbol B in FIG. 8) and concentration level of the sample reaches the threshold level, the sample detection signal b may be generated. However, in this stage, as the sample detection inhibiting timer 21 is in the on-state and therefore sample dection permitting timer 22 is in the off-state the shifting timer start signal generator 23 will never generate the signal. In case of the sample at the higher concentration out of the samples $a_1$ and $a_2$ shown in FIG. 8, output from the sample does not reach the threshold level and the sample detection signal b is not generated accordingly.

As is described above, the sample detection signal b is not generated in either case of the low-concentration sample $a_1$ or high-concentration sample $a_2$. In these cases, the shifting timer start signal generator 23 generates the signal e when the signal from the sample detection permitting timer 22 is switched from on to off, and the signal c of the shifting timer 18 is turned on by the signal e. When a predetermined time lapses after the signal c has been turned on, the timer 18 is switched from on to off, and the signal d provided at that time from the carrier shifting controller 19 functions to stop the carrier shifting mechanism 20. Accordingly, the carrier is stopped at a position advanced by a predetermined distance l. Therefore, as described above, the sample is located at the position of the optical axis of the photometric system to make it possible to perform photometry of the sample. When individual samples are arranged at constant pitches on a carrier, for example, in case of a carrier onto which samples are applied at constant pitches with a sample applicator for electrophoresis or by manual method, it is possible to perform photometry with the carrier kept stopped when a sample is located at the position of the optical axis of the photometric system by the method according to the present invention whether or not the sample is normal.

In the embodiment described above, the timing to turn on the shifting timer is different between the two cases: one where the shifting timer is operated by the sample detection signal b produced when rear end of a sample is detected and the other where the shifting timer is operated without detecting a sample which is not normal when the sample detection permitting timer is switched from on to off. On the other hand, since the shifting timer is turned on at constant time intervals, sample position at the stop time of the carrier is different between samples which are normal and not normal respectively. The operating time intervals of the shifting timer are made coincident with the time intervals for shifting the carrier from detection of rear end of a sample to alignment of the sample center with the optical axis of the photometric system. Therefore, in case of a sample which is not normal, the carrier is stopped at a position where the sample center is not aligned with the optical axis of the photometric system. For example, if sample end detection time T is located in the middle of the section $T_1-T_2$ in which the sample detection permitting timer is kept on, the carrier is stopped at such a position that the sample center is shifted beyond the optical axis by a distance corresponding to $(T_2-T)/2$. However, no hindrance is caused for photometry since the sample is substantially the same concentration over an area rather wide around the center of the sample. When plural samples which are not normal appear successively, however, sum of such deviations will cause undesirable results.

Figure 9:
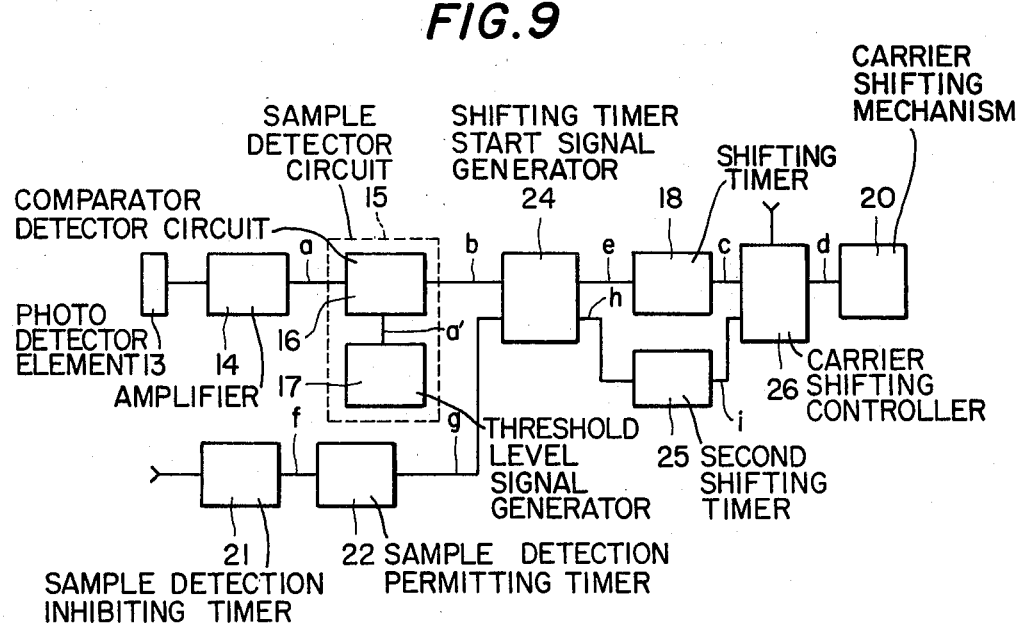
FIG. 9 illustrates a block diagram showing a second embodiment of the present invention.

FIG. 9 shows a second embodiment of the present invention which is improved so as to be capable of correcting the above-mentioned defect. This embodiment is different from the first embodiment in that it uses a shifting timer start signal generator 24 which is different from that used in the first embodiment, in combination with a second shifting timer having an operation time 25 which is different from that of the shifting timer 18, the other points substantially being the same as those in the first embodiment. Speaking concretely, when the sample detection signal b is inputted with the sample detection permitting timer 22 kept on, the shifting timer start signal generator 24 generates the shifting timer start signal e, which is inputted to the shifting timer 18 to stop the carrier shifting mechanism 20 at falling time of the signal c from the timer 18 is in the same manner as that in the first embodiment. If the signal b is not inputted to the shifting timer start signal generator 24 while the sample detection permitting timer 22 is kept on, the shifting timer start signal generator 24 generates a signal h which is inputted to the second shifting timer 25. With the signal input to the second shifting timer 25, a timer signal i is emitted at a timing different from that by the timer 18 and the signal d from a carrier shifting controller 26 falls down at the falling time of the signal i, thereby stopping the carrier shifting mechanism 20. Now, operations of the second embodiment of the present invention will be described with reference to FIG. 10 and FIG. 11. In the first place, detection of a normal sample will be described referring to FIG. 10. In case of a normal sample, the signal from the shifting timer start signal generator 24 is same as the signal e in the first embodiment and the signal h is not generated. Therefore, when the signal c from the shifting timer 18 is switched from on to off, the carrier shifting operation is stopped and the carrier is stopped at the position at which the sample center is aligned with the optical axis of the photometric system in the same manner as that in the first embodiment. In case of a sample which is not normal, the sample detection signal b is not generated as shown in FIG. 11. Therefore, the shifting timer start signal generator 24 does not generate the signal e and the timer 18 does not operate. Inversely, the shifting timer start signal generator 24 generates the signal h when the signal g from the sample detection permitting timer 22 is switched from on to off. With the generation of the signal h, the second shifting timer 25 generates the signal i. When the time interval of this signal i is set so as to be different from (shorter than) that of the signal c from the shifting timer 18, the signal i from the second shifting timer 25 is switched from on to off earlier than the timing when the shifting timer 18 is switched from on to off in case of a sample which is not normal in the first embodiment. Since the signal d is generated to stop the carrier shifting mechanism 20 the moment that the signal i is switched from on to off, the carrier is stopped earlier in the second embodiment than in the first embodiment. Therefore, the second embodiment makes it possible to compensate the positional deviation caused in case of a sample which is not normal in the first embodiment. The time interval for the second shifting timer is to be set for a time difference which is equal to the time interval for the timer 18 minus the time interval as measured from the generation time T of the sample detection signal b to the falling time $T_2$ of the signal g from the sample detection permitting timer 22. If T is located in the middle between $T_1$ and $T_2$, for example, the time interval for the second shifting timer is to be set at $(T_2-T_1)/2$. This time interval is determined depending on settings of $T_1$ and $T_2$, the latter being especially important. Therefore, it is possible in any cases to stop the carrier at such a position that the optical axis of the photometric system is aligned substantially with the center of a sample by selecting the time interval for the second timer at an adequate value. As is understood from the foregoing descriptions, the method according to the present invention makes it possible to stop the carrier when a sample is located at the position of the optical axis of a photometric system even if a sample detection signal is not generated due to too high or low concentration of the sample. Further, the second embodiment of the present invention makes it possible to stop the carrier at all time when the center of a sample is substantially aligned with the optical axis of a photometric system. It is therefore capable of stopping the carrier when a sample is located on the optical axis of the photometric system even when samples which are not normal appear successively. Furthermore, arrangement of a sample detection inhibiting timer makes it possible to stop the carrier at such a position that center of a sample is aligned substantially when the optical axis of the photometric system even when concentration of the sample is nearly equal to the threshold level. Therefore, the present invention makes it possible to stop the carrier when a sample is aligned with the optical axis of the photometric system regardless of sample conditions, thereby eliminating the possibility to skip samples so as to perform photometry without fail and to cause erroneous transfer of analytical results.

We claim:

1. A sample centering system comprising a photometric means for colorimetrically measuring samples applied onto a carrier shifted in a certain definite direction, a sample detecting means arranged at a definite interval apart from said photometric means in the carrier shifting direction, a sample detection signal generating means connected to said sample detecting means and capable of generating a first signal when the output from said sample detecting means varies so as to be coincident with a predetermined threshold level, a shifting timer start signal generator means connected to said sample detection signal generating means and capable of generating a second signal, a sample detection permitting timer means connected to said shifting timer start signal generator means and capable of commencing operation at a predetermined definite time after shifting of said carrier is started and having a first predetermined definite operation time, a sample detection inhibiting timer means connected to said sample detection permitting timer means and capable of inhibiting sample detection during a predetermined definite time after shifting of said carrier is started, a shifting timer connected to said shifting timer start signal generator means and capable of commencing operation when said second signal is put in and having a second predetermined definite operation time to generate a third signal, a carrier shifting controller connected to said shifting timer and capable of being operated by said third signal, and a carrier shifting mechanism connected to said carrier shifting controller and capable of stopping said carrier with a signal from said carrier shifting controller, said second signal being generated when said first signal is generated if said first signal is generated within said first predetermined definite operation time, or when said first predetermined definite operation time has lapsed if said first signal is not generated within said first predetermined definite operation time.

2. A sample centering system comprising a photometric means for colorimetrically measuring samples applied onto a carrier shifted in a certain definite direction, a sample detecting means arranged at a definite interval apart from said photometric means in the carrier shifting direction, a sample detection signal generating means connected to said sample detecting means and capable of generating a first signal when the output from said sample detecting means varies so as to be coincident with a predetermined threshold level, a shifting timer start signal generator means connected to said sample detection signal generating means and capable of generating a second signal and third signal, a sample detection permitting timer means connected to said shifting timer start signal generator means and capable of commencing operation at a predetermined definite time after shifting of said carrier is started and having a first predetermined definite operation time, a sample detection inhibiting timer means connected to said sample detection permitting timer means and capable of inhibiting sample detection during a predetermined definite time after shifting of said carrier is started, a first shifting timer connected to said shifting timer start signal generator means and capable of commencing operation only when said second signal is put in and having a second predetermined definite operation time to generate a fourth signal, a second shifting timer connected to said shifting timer start signal generator means and capable of commencing operation only when said third signal is put in and having a third predetermined definite operation time shorter than said second predetermined definite operation time to generate said fifth signal, a carrier shifting controller connected to said first and second shifting timers and capable of being operated by any one of said fourth and fifth signals and a carrier shifting mechanism connected to said carrier shifting controller and capable of stopping said carrier with a signal from said carrier shifting controller, said second signal being generated when said first signal is generated if said first signal is generated within said first predetermined definite operation time, and said third signal being generated when said first predetermined definite operation time has lapsed if said first signal is not generated within said first predetermined definite operation time.

* * * * *